United States Patent [19]

Johnson

[11] 4,202,972
[45] May 13, 1980

[54] Δ²-PROSTACYCLIN ANALOGS

[75] Inventor: Roy A. Johnson, Kalamazoo, Mich.

[73] Assignee: The Upjohn Company, Kalamazoo, Mich.

[21] Appl. No.: 936,295

[22] Filed: Aug. 23, 1978

Related U.S. Application Data

[63] Continuation-in-part of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.² .......................................... C07D 311/02
[52] U.S. Cl. .............................. 542/426; 260/345.2; 542/429
[58] Field of Search .................... 260/345.2; 542/426, 542/429

[56] References Cited

PUBLICATIONS

Pace-Asciak et al., Biochem., 10, 3657 (1971).
Pace-Asciak et al., JACS, 98, 2348 (1976).

*Primary Examiner*—Nicky Chan
*Attorney, Agent, or Firm*—Robert A. Armitage

[57] ABSTRACT

Enlarged-hetero-ring prostacyclin analogs having a Δ² feature are disclosed, for example

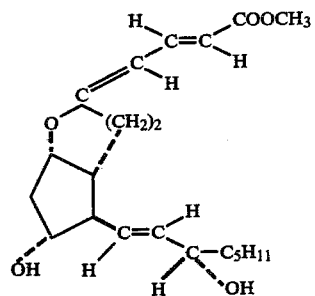

said analogs having pharmacological activity. Processes for preparing them and the appropriate intermediates are disclosed.

32 Claims, No Drawings

Δ²-PROSTACYCLIN ANALOGS

CROSS REFERENCE TO RELATED APPLICATIONS

This application is a continuation-in-part of copending application Ser. No. 819,856, filed July 28, 1977, issued as U.S. Pat. No. 4,123,441, which was a continuation-in-part of then copending application Ser. No. 725,546, filed Sept. 22, 1976 since abandoned which was a continuation-in-part of then copending application Ser. No. 716,960, filed Aug. 23, 1976, since abandoned.

BACKGROUND OF THE INVENTION

This invention relates to certain heterocyclic organic compounds, namely prostacyclin analogs and to processes for preparing them.

Prostacyclin and prostacyclin-type compounds are well-known organic compounds. Prostacyclin ($PGI_2$) is represented by the formula for which see R. A. Johnson et al., J. Am. Chem. Soc. 99, 4182 (1977). Other prostacyclin-type compounds are disclosed by R. A. Johnson et al., Prostaglandins 15, No. 5, 737–740 (1978) and in Belg. Patents No. 851,122, 855,224, 859,057, and 860,278. See, respectively, Derwent Farmdoc Abstract Nos. 57511Y, 86540Y, 25186A, and 32096A.

Detailed background for this application will be found in U.S. patent application Ser. No. 819,856, filed July 28, 1977 issued as U.S. Pat. No. 4,123,441 which is incorporated herewith by reference in its entirety under the provisions of M.P.E.P. 608.01(p). Therein is also a statement of the utility of these compounds, alternate processes of synthesis, and complete description of starting materials useful herein.

SUMMARY OF THE INVENTION

It is the purpose of this invention to provide novel products having pharmacological activity. It is a further purpose to provide processes for preparing those products and their intermediates. More specifically, there are provided Δ² enlarged-hetero-ring prostacyclin analogs.

Accordingly there are provided (4Z) compounds of the formula wherein the terms Q, $R_1$, etc. are defined herein in the TABLE of Definition of Terms for Formulas.

TABLE
DEFINITION OF TERMS FOR FORMULAS

Q is wherein $R_8$ is hydrogen or alkyl of one to 4 carbon atoms, inclusive.

$Q_3$ is wherein $R_8$ is hydrogen or alkyl of one to 4 carbon atoms, inclusive.

$Q_4$ is wherein $R_8$ is hydrogen or alkyl of one to 4 carbon atoms, inclusive, and $R_{24}$ is (a) tetrahydropyranyl, (b) tetrahydrofuranyl, or (c) a group of the formula wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, —$(CH_2)_a$— or —$(CH_2)_b$—O—$(CH_2)_c$— wherein a is 3, 4, 5, b is one, 2, or 3, and c is one, 2, or 3 with the proviso that b plus c is 2, 3, or 4, and wherein $R_{17}$ is hydrogen or phenyl.

$R_1$ is
(1) —$COOR_3$
(2) —$CH_2OH$
(3) —$CH_2N(R_9)(R_{18})$ $$-\overset{\overset{\displaystyle O}{\|}}{C}-N(R_9)(R_{18}) \text{ or} \quad (4)$$

$$-\overset{|}{C}\diagdown\underset{N\text{---}N}{\overset{NH\text{---}N}{\diagup}} \quad (5)$$

wherein $R_3$ is (a) hydrogen, (b) alkyl of one to 12 carbon atoms, inclusive (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive, (g) $-\text{C}_6\text{H}_4-\text{NH}-\overset{\overset{\displaystyle O}{\|}}{C}-\text{C}_6\text{H}_4-\text{NH}-\overset{\overset{\displaystyle O}{\|}}{C}-\text{CH}_3,$ (h) $-\text{C}_6\text{H}_4-\text{NH}-\overset{\overset{\displaystyle O}{\|}}{C}-\text{C}_6\text{H}_5,$ (i) $-\text{C}_6\text{H}_4-\text{NH}-\overset{\overset{\displaystyle O}{\|}}{C}-\text{CH}_3,$ (j) $-\text{C}_6\text{H}_4-\text{NH}-\overset{\overset{\displaystyle O}{\|}}{C}-\text{NH}_2,$ (k) $-\text{C}_6\text{H}_4-\text{CH}=\text{N}-\text{NH}-\overset{\overset{\displaystyle O}{\|}}{C}-\text{NH}_2,$ (l) 2-naphthyl, (m) $-\underset{\underset{\displaystyle R_{11}}{|}}{\text{CH}}-\overset{\overset{\displaystyle O}{\|}}{C}-R_{10}$ wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive.

$R_4$ is $$-\underset{\underset{\displaystyle R_6}{|}}{\overset{\overset{\displaystyle R_5}{|}}{C}}-C_gH_{2g}-CH_3 \quad (1)$$

$$-\underset{\underset{\displaystyle R_6}{|}}{\overset{\overset{\displaystyle R_5}{|}}{C}}-Z-\text{C}_6\text{H}_{4}(T)_s \text{ or} \quad (2)$$

$$-\text{CH}_2\diagdown\underset{\underset{\displaystyle H}{}}{\overset{\overset{\displaystyle}{}}{C}}=\overset{\overset{\displaystyle}{}}{\underset{\underset{\displaystyle H}{}}{C}}\diagup\text{CH}_2\text{CH}_3 \quad (3)$$

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxo atom (—O—) or $C_jH_{2j}$ is a valence bond or alkylene of one to 9 carbon atoms, inclusive, with one to 6 carbon atoms, inclusive between $CR_5R_6$- and the phenyl ring; wherein T is alkyl of one to 4 carbon atoms, inclusive, fluoro, chloro, trifluoromethyl, or $-OR_7$- wherein $R_7$ is alkyl of one to 4 carbon atoms, inclusive, and s is zero, one, 2 or 3, with the proviso that not more than two T's are other than alkyl and when s is 2 or 3 the T's are either the same or different.

$R_{12}$ is alkyl of one to 4 carbon atoms, inclusive.

$R_{19}$ is chloro, bromo, or iodo.

$(R_{20})$ is [cyclopentane structures with OH, OH, =O, =CH$_2$, and others with CH$_2$OH]

$(R_{22})$ is [cyclopentane structures with OH, OH, or others]

$(R_{23})$ is [cyclopentane structures with OR$_{24}$, OR$_{24}$, or others]

wherein $R_{24}$ is (a) tetrahydropyranyl, (b) tetrahydrofuranyl, or (c) a group of the formula $$R_{14}-O-\underset{\underset{\displaystyle R_{15}}{|}}{\overset{\overset{\displaystyle |}{}}{C}}-\underset{\underset{\displaystyle R_{16}}{|}}{\overset{\overset{\displaystyle H}{|}}{C}}-R_{17}$$

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, $-(CH_2)_a-$ or $-(CH_2)_b-O-(CH_2)_c-$ wherein a is 3, 4, 5, b is one, 2, or 3, and c is one, 2, or 3 with the proviso that b plus c is 2, 3, or 4, and wherein $R_{17}$ is hydrogen or phenyl.

$R_{24}$ is as defined immediately above.

X is
(1) trans—CH=CH—
(2) cis—CH=CH—
(3) —C≡C— or
(4) —CH$_2$CH$_2$—.

The symbol ~ (wavy line) indicates attachment in alpha or beta configuration.

END OF TABLE

There are also provided (4E) compounds of the formula

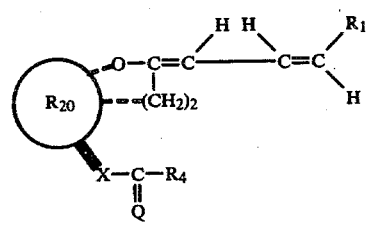

XLI

As to "Z" and "E" nomenclature see J. E. Blackwood et al., J. Am. Chem. Soc. 90, 509 (1968).

Chart E shows a preferred process for preparing $\Delta^2$-prostacyclin analogs XXXVIII with the scope of formula XL. All terms such as $Q_3$, $R_4$, etc. are as defined in the TABLE included herein. The starting materials of formula XXXIII are available by methods disclosed in the predecessor application and are within the scope of 4-halo compounds of formula III described therein.

In step (a), compounds XXXIV are formed by blocking C-11 and C-15 hydroxyls of the formula XXXIII compounds. When the blocking group, $R_{24}$ is tetrahydropyranyl or tetrahydrofuranyl, the appropriate reagent, e.g., 2,3-dihydropyran or 2,3-dihydrofuran, is used in an inert solvent such as dichloromethane, in the presence of an acid condensing agent such as p-toluene solfonic acid or pyridine hydrochloride. The reagent is used in slight excess, preferably 1.0 to 1.2 times theory. The reaction is carried out at about 20°–50° C.

When the blocking group is of the formula

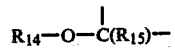

CHR$_{16}$R$_{17}$, the appropriate reagent is a vinyl ether, e.g., ethyl vinyl ether, isobutyl vinyl ether or any vinyl ether of the formula R$_{14}$—O—C(R$_{15}$)=CR$_{16}$R$_{17}$ wherein R$_{14}$, R$_{15}$, R$_{16}$, and R$_{17}$

CHART E

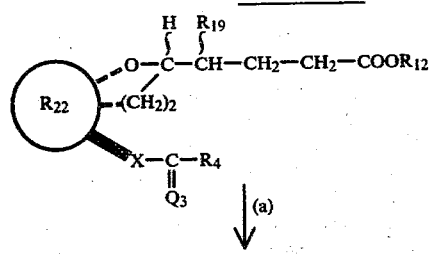

XXXIII

CHART E

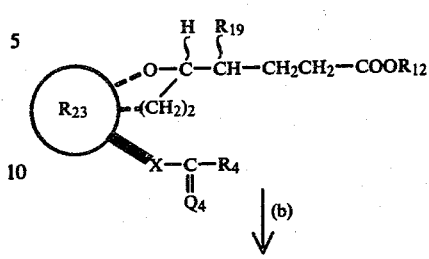

XXXIV (b)

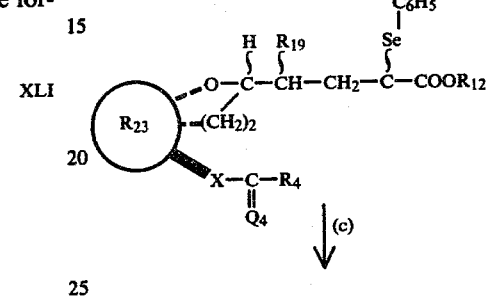

XXXV (c)

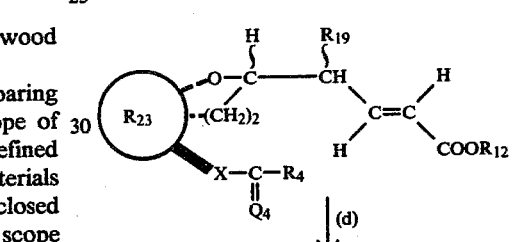

XXXVI (d)

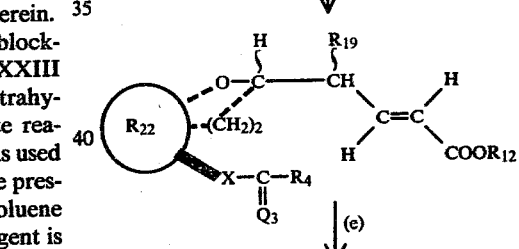

XXXVII (e)

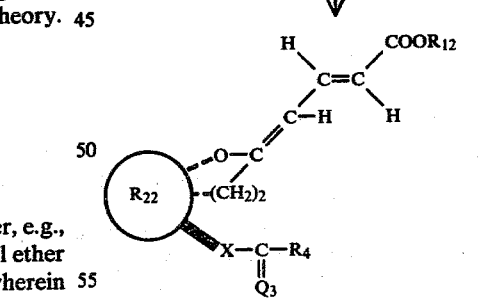

XXXVIII are as defined herein; or an unsaturated cyclic or heterocyclic compound, e.g., 1-cyclohex-1-yl methyl ether

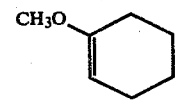

or 5,6-dihydro-4-methoxy-2H-pyran

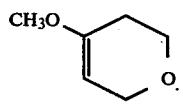

In step (b), the formula-XXXV selenide derivatives are prepared. For background on preparing $\Delta^2$-prostaglandin analogs by an analogous method, see for example U.S. Pat. No. 4,024,174. The compounds of formula XXXIV are transformed first to 2-lithium derivatives, for example by reaction with a lithium amide formed from a secondary amine such as N-isopropylcyclohexylamine. It is preferred that that reaction be done at a low temperature, as in a Dry Ice bath. Thereafter the formula-XXXV compounds are obtained by reaction with diphenyldiselenide or benzeneselenyl bromide using about 3 equivalents for each molecular equivalent of the C-2 lithium derivative. Here again the preferred temperature is about $-78°$ C.

In step (c) the formula-XXXVI $\Delta^2$ intermediates are formed by oxidative elimination. Hydrogen peroxide or sodium periodate are useful.

In step (d) the $R_{24}$ blocking groups are replaced, as by mild acid hydrolysis, to yield the XXXVII intermediates.

Finally in step (e) the formula-XXXVIII enol ethers, i.e. $\Delta^2$ prostacyclin analogs, are obtained by dehydrohalogenation using any of the reagents and conditions known in the art for the prostacyclins, as fully described in the predecessor application. For example, the formula-XXXVII 4-halo compound is treated with a tertiary amine such as 1,5-diazabicyclo[4.3.0]non-5-ene ("DBN") at about 40° C. In a solvent.

Salts such as the preferred alkali metal salts, including sodium, potassium or lithium salts, are obtained simply by saponification of any of these $R_{12}$ lower alkyl esters, such as the methyl ester, under mild conditions.

Other compounds within the scope of formula XL are obtained by transformations known in the art. For example, other esters are obtained by transesterification or by selection of suitable starting materials or intermediates with the desired ester groups. Amides within the scope of $R_1$ are obtained by replacing the formula-XXXIII starting material with corresponding 4-halo amides. Compounds wherein $R_{20}$ is other than $R_{22}$ are obtained by known transformations. Thus, the intermediates of formula XXXVI or XXXVII may be converted to $\Delta^{10}$ compounds, or to 11-hydroxymethyl compounds, or to 11-methylene compounds and finally to the desired formula-XL compound by transformations shown herein or in the predecessor referenced application, or known in the art. Likewise, other forms of Q are obtained by transforming these intermediates or final products. Various forms of $R_4$ or X are obtained by using the appropriate formula-XXX 4-halo starting materials which are derived from the corresponding $PGF_{2\alpha}$ analogs.

The amides are also conveniently prepared by reaction of ammonia or an amine with a mixed anhydride obtained from the sodium salts. The anhydride may be prepared by the reaction of isobutylchloroformate in the presence of a tertiary amine.

The (4E) compounds are obtained by replacing the starting materials of Chart E with 4-halo compounds derived from the corresponding trans-$\Delta^4$-$PGF_{2\alpha}$ compounds.

DESCRIPTION OF THE PREFERRED EMBODIMENTS

The invention is further illustrated by, but not limited to, the following examples.

All temperatures are in degrees centigrade.

"Brine," herein, refers to an aqueous saturated sodium chloride solution.

Chromatography, as used herein, is understood to be chromatography on a silica gel column, and to include elution, collection of fractions, and combinations of those fractions shown by TLC (thin layer chromatography) to contain the desired product free of starting material and impurities.

"Drying", as used herein, refers to contacting a compound, in solution, with an anhydrous agent such as sodium sulfate or magnesium sulfate to remove water, followed by filtering to remove solids.

"Concentrating" as used herein, refers to concentration under reduced pressure, preferably at less than 50 mm. and at temperatures below 35° C.

Examples 1–33 are in U.S. Pat. No. 4,123,441, incorporated here by reference.

EXAMPLE 34

(4Z)-9-Deoxy-5,9α-epoxy-$\Delta^4$-trans-66 $^2$-$PGF_1$, Methyl Ester. (Formula XXXVIII)

I. Refer to Chart E. There is first prepared XXXIV, the 11,15-bis(tetrahydropyran-2-yl ether) of the formula-XXXIII iodo compound. The (4R,5R)-4-iodo-9-deoxy-5,9α-epoxy-$PGF_1$, methyl ester of Example 6 of the parent application is reacted with excess dihydropyran in methylene chloride in the presence of pyridine hydrochloride at about 25° C. for 6 hr. The reaction mixture is washed with aqueous potassium bicarbonate solution, dried, and concentrated.

II. The formula-XXXV selenide derivative is next prepared. To a solution of n-isopropylcyclohexylamine (8.27 mmol) in 30 ml of tetrahydrofuran at $-78°$, under nitrogen, is added n-butyllithium (4.7 ml, 7.52 mmol, 1.6 in hexane) via syringe. The mixture is stirred for 15 min. and to it is added the product of step I above (3.76 mmol) in 10 ml. of tetrahydrofuran and stirring is continued at $-78°$ C. for an additional 30 min. Diphenyl diselenide (5.64 mmol) in 15 ml. of tetrahydrofuran is then added to the reaction mixture. After stirring at $-78°$ for an additional hour, the Dry Ice bath is removed and the reaction mixture allowed to warm up to 0°. The resulting mixture is poured into 150 ml of saturated aqueous ammonium chloride and 150 ml. of ether. The ether layer is separated and the aqueous layer extracted with ether (800 ml total). The combined ether extracts are washed successively with 40 ml of ice water and 30 ml. of saturated brine. The organic extract is dried over $Na_2SO_4$ and concentrated in vacuo to yield crude 2-phenyl-selenide derivative.

III. The formula-XXXVI $\Delta^2$ compound is next prepared. A solution of the selenide derivative of part II above (2.88 mmol) in 65 ml. of methylene chloride is treated at about 25° C. with hydrogen peroxide (29 mmol) as a 10% aqueous solution and stirred for one hr. The organic phase is separated, washed with 5% sodium bicarbonate, saturated sodium bicarbonate, and brine, dried, and concentrated. The residue is chromatographed to yield the $\Delta^2$ compound.

IV. The THP blocking groups are next removed. The product of Part III is treated at 40° C. with methanoltetrahydrofuran-water-acetic acid (42:35:21:2) for 4 hr. The mixture is concentrated and again concentrated using benzene as an azeotropic agent. The resulting oily residue is chromatographed to yield the formula-XXXVII compound.

V. The title compound is obtained by dehydrohalogenation. The formula-XXXVII iodo ether of Part IV above (1.20 mmol) is dissolved in 33 ml. of benzene and treated with 1.2 ml. of 1,5-diazo-bicyclo[4.3.0]non-5-ene at 40° C. for 1.75 hr. The mixture is cooled to about 25° C., washed with ice water and dried to yield the title compound.

EXAMPLE 35

(4Z)-9-Deoxy-5,9α-epoxy-Δ⁴-trans-Δ²PGF₁, Sodium Salt.

A solution of the methyl ester (Example 34), (0.41 mmole) in 5 ml. of methanol is treated with aqueous 0.05 N. sodium hydroxide (9.0 ml., 0.45 mmole). The mixture is stirred at about 25° C. for 48 hr. The mixture is concentrated to remove methanol. The remaining aqueous solution is freeze-dried to yield the title compound.

Following the procedures of Examples 34 and 35, but replacing the formula-XXXIII starting material with the appropriate compound, there are prepared for the following compounds, which are methyl esters and sodium salts of the respective prostacyclin analogs:

(4Z)-9-deoxy-5,9α-epoxy-Δ⁴-trans-Δ²-15(S)-15-methyl-PGF₁, methyl ester and sodium salt (4Z)-9-deoxy-5,9α-epoxy-Δ⁴-trans-Δ²-16,16-dimethyl-PGF₁, methyl ester and sodium salt (4Z)-9-deoxy-5,9α-epoxy-Δ⁴-trans-Δ²-13,14-dihydro-PGF₁, methyl ester and sodium salt (4Z)-9-deoxy-5,9α-epoxy-Δ⁴-trans-Δ²-17-phenyl-18,19,20-trinor-PGF₁, methyl ester and sodium salt (4Z)-9-deoxy-5,9α-epoxy-Δ⁴-trans-Δ²-16-phenoxy-17,18,19,20-tetranor-PGF₁, methyl ester and sodium salt (4Z)-9-deoxy-5,9α-epoxy-Δ⁴-trans-Δ²-16-(m-chlorophenoxy)-17,18,19,20-tetranor-PGF₁, methyl ester and sodium salt (4Z)-9-deoxy-5,9α-epoxy-Δ⁴-trans-Δ²-16-(α,α,α-trifluoro-p-tolyloxy)-17,18,19,20-tetranor-PGF₁, methyl ester and sodium salt (4Z)-9-deoxy-5,9α-epoxy-Δ⁴-trans-Δ²-13,14-dihydro-16-phenoxy-17,18,19,20-tetranor-PGF₁, methyl ester and sodium salt (4E)-9-deoxy-5,9α-epoxy-Δ⁴-trans-Δ²-PGF₁, methyl ester and sodium salt

EXAMPLE 36

(4Z)-9-deoxy-5,9α-epoxy-Δ⁴-trans-Δ²-PGF₁, Amide (Formula XL)

The mixed anhydride is prepared by treating a suspension of the corresponding sodium salt (Example 35) in methylene chloride with a slight excess of isobutylchloroformate in the presence of triethylamine at about 0° C. and continuing the reaction at about 25° C. until the anhydride is formed. Thereafter the mixture is cooled to 0° C. and treated with gaseous ammonia. The mixture is then warmed to 25° C. and filtered. The filtrate is concentrated, then taken up in ethyl acetate and water. The organic phase is washed with water, dried, and concentrated to give the title compound.

Following the procedures of Example 36 but replacing that sodium salt with the appropriate sodium salt, the following amides are prepared:

4(Z)-9-deoxy-5,9α-epoxy-Δ⁴-trans-Δ²-PGF₁, amide
4(Z)-9-deoxy-5,9α-epoxy-Δ⁴-trans-Δ²-13,14-dihydro-16-phenoxy-17,18,19,20-tetranor-PGF₁, amide
4(E)-9-deoxy-5,9α-epoxy-Δ⁴-trans-Δ²-PGF₁, amide.

I claim:

1. A 4Z compound of the formula

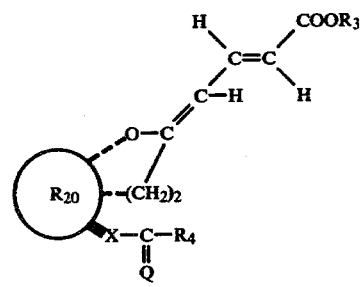

wherein $R_{20}$ is

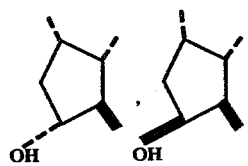

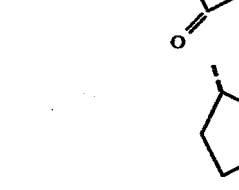

wherein Q is

wherein
$R_8$ is hydrogen or alkyl of one to 4 carbon atoms, inclusive, wherein
$R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

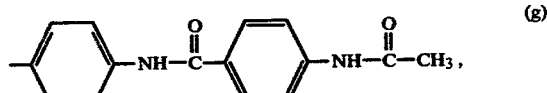

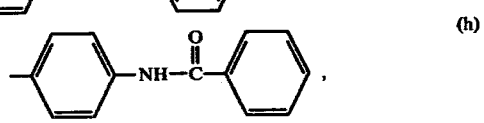

-continued

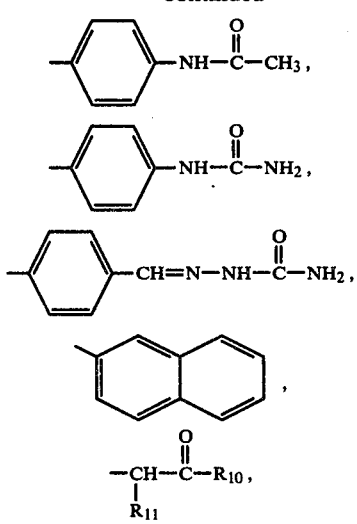

wherein
R₁₀ is phenyl, p-bromophenyl, p-biphenylyl, p-nitrophenyl, p-benzamidophenyl, or 2-naphthyl, and wherein R₁₁ is hydrogen or benzoyl, or (n) a pharmacologically acceptable cation;
wherein
R₄ is

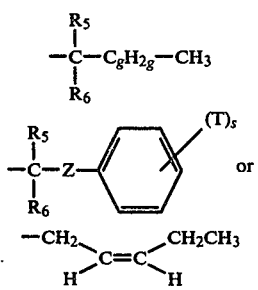

wherein
$C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—);
wherein
Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between CR₅R₆— and the phenyl ring;
wherein
T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different; and
wherein
X is (1) trans—CH=CH—
(2) cis—CH=CH—
(3) —C≡C— or
(4) —CH₂CH₂—;
including the lower alkanoates thereof.

2. A compound according to claim 1 wherein Q is

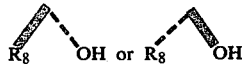

wherein
R₈ is hydrogen or alkyl of one to 4 carbon atoms, inclusive, and R₂₀ is

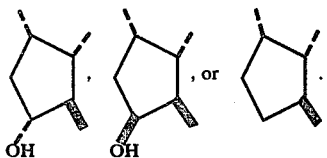

3. A compound according to claim 2 wherein R₂₀ is

4. A compound according to claim 3 wherein Q is

wherein R₈ is hydrogen, methyl, or ethyl.

5. A compound according to claim 4 wherein R₄ is

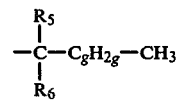

wherein $C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro.

6. A compound according to claim 4 wherein R₄ is

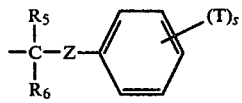

wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro, chloro, trifluoromethyl, or $-OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different.

7. A compound according to claim 1 wherein $R_3$ is (a) hydrogen, (b) alkyl of one to 12 carbon atoms, inclusive, or (c) a pharmacologically acceptable cation.

8. A compound according to claim 7 wherein $R_3$ is methyl or sodium.

9. (4Z)-9-Deoxy-5,9α-epoxy-$\Delta^4$-trans-$\Delta^2$-PGF$_1$, methyl ester, a compound according to claim 8.

10. (4Z)-9-Deoxy-5,9α-epoxy-$\Delta^4$-trans-$\Delta^2$-PGF$_1$, sodium salt, a compound according to claim 8.

11. (4Z)-9-Deoxy-5,9α-epoxy-$\Delta^4$-trans-$\Delta^2$-(15S)-15-methyl-PGF$_1$, methyl ester, a compound according to claim 8.

12. (4Z)-9-Deoxy-5,9α-epoxy-$\Delta^4$-trans-$\Delta^2$-(15S)-15-methyl-PGF$_1$, sodium salt, a compound according to claim 8.

13. (4Z)-9-Deoxy-5,9α-epoxy-$\Delta^4$-trans-$\Delta^2$-16,16-dimethyl-PGF$_1$, methyl ester, a compound according to claim 8.

14. (4Z)-9-Deoxy-5,9α-epoxy-$\Delta^4$-trans-$\Delta^2$-16,16-dimethyl-PGF$_1$, sodium salt, a compound according to claim 8.

15. (4Z)-9-Deoxy-5,9α-epoxy-$\Delta^4$-trans-$\Delta^2$-13,14-dihydro-PGF$_1$, methyl ester, a compound according to claim 8.

16. (4Z)-9-Deoxy-5,9α-epoxy-$\Delta^4$-trans-$\Delta^2$-13,14-dihydro-PGF$_1$, sodium salt, a compound according to claim 8.

17. A compound according to claim 12 wherein $R_3$ is (a) hydrogen, (b) alkyl of one to 12 carbon atoms, inclusive, or (c) a pharmacologically acceptable cation.

18. A compound according to claim 17 wherein $R_3$ is methyl or sodium.

19. (4Z)-9-Deoxy-5,9α-epoxy-$\Delta^4$-trans-$\Delta^2$-17-phenyl-18,19,20-trinor-PGF$_1$, methyl ester, a compound according to claim 18.

20. (4Z)-9-Deoxy-5,9α-epoxy-$\Delta^4$-trans-$\Delta^2$-17-phenyl-18,19,20-trinor-PGF$_1$, sodium salt, a compound according to claim 18.

21. (4Z)-9-Deoxy-5,9α-epoxy-$\Delta^4$-trans-$\Delta^2$-16-phenoxy-17,18,19,20-tetranor-PGF$_1$, methyl ester, a compound according to claim 18.

22. (4Z)-9-Deoxy-5,9α-epoxy-$\Delta^4$-trans-$\Delta^2$-16-phenoxy-17,18,19,20-tetranor-PGF$_1$, sodium salt, a compound according to claim 18.

23. (4Z)-9-Deoxy-5,9α-epoxy-$\Delta^4$-trans-$\Delta^2$-16-(m-chlorophenoxy)-17,18,19,20-tetranor-PGF$_1$, methyl ester, a compound according to claim 22.

24. (4Z)-9-Deoxy-5,9α-epoxy-$\Delta^4$-trans-$\Delta^2$-16-(m-chlorophenoxy)-17,18,19,20-tetranor-PGF$_1$, sodium salt, a compound according to claim 18.

25. (4Z)-9-Deoxy-5,9α-epoxy-$\Delta^4$-trans-$\Delta^2$-16-(α,α,α-trifluoro-p-tolyloxy)-17,18,19,20-tetranor-PGF$_1$, methyl ester, a compound according to claim 18.

26. (4Z)-9-Deoxy-5,9α-epoxy-$\Delta^4$-trans-$\Delta^2$-16-(α,α,α-trifluoro-p-tolyloxy)-17,18,19,20-tetranor-PGF$_1$, sodium salt, a compound according to claim 18.

27. (4Z)-9-Deoxy-5,9α-epoxy-$\Delta^4$-trans-$\Delta^2$-13,14-dihydro-16-phenoxy-17,18,19,20-tetranor-PGF$_1$, methyl ester, a compound according to claim 18.

28. (4Z)-9-Deoxy-5,9α-epoxy-$\Delta^4$-trans-$\Delta^2$-13,14-dihydro-16-phenoxy-17,18,19,20-tetranor-PGF$_1$, sodium salt, a compound according to claim 18.

29. A 4E compound of the formula

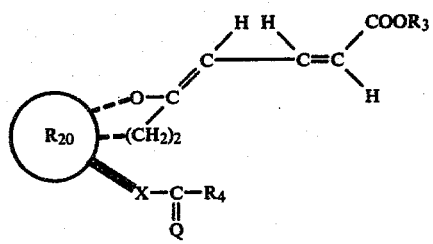

wherein $R_{20}$ is

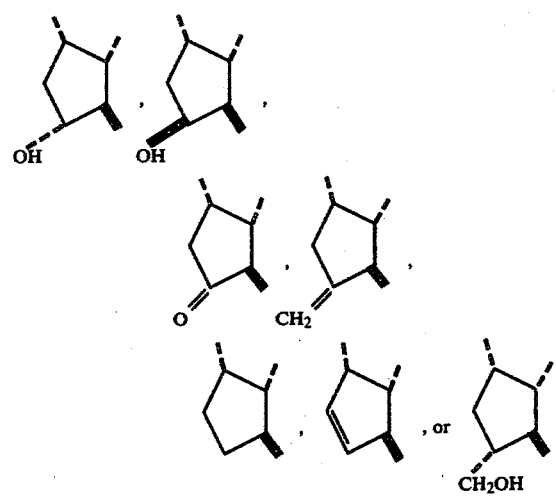

wherein
Q is

wherein
$R_8$ is hydrogen or alkyl of one to 4 carbon atoms, inclusive,
wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

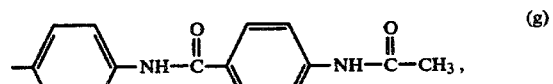

(g)

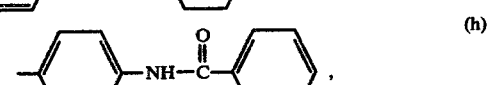

(h)

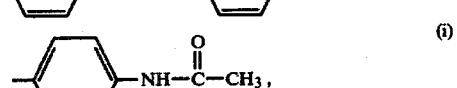

(i)

-continued

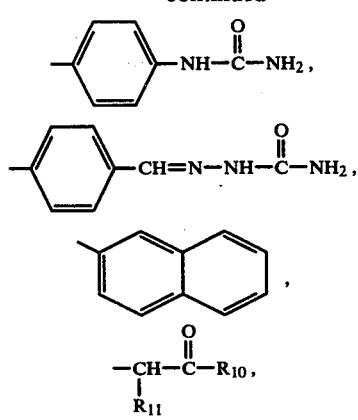
(j)

(k)

(l)

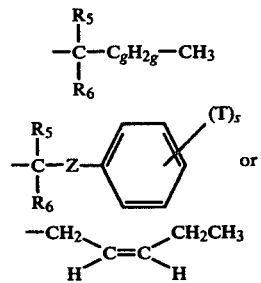
(m)

wherein
R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation;
wherein R$_4$ is $$-\underset{R_6}{\overset{R_5}{C}}-C_gH_{2g}-CH_3 \quad (1)$$

$$-\underset{R_6}{\overset{R_5}{C}}-Z-\text{[phenyl](T)}_s \text{ or} \quad (2)$$

$$-CH_2\underset{H}{\overset{}{C}}=C\underset{H}{\overset{}{-}}CH_2CH_3 \quad (3)$$

wherein
C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);
wherein
Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring;

wherein
T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and
wherein
X is
(1) trans—CH=CH—
(2) cis—CH=CH—
(3) —C≡C— or
(4) —CH$_2$CH$_2$—;
including the lower alkanoates thereof.

30. A compound according to claim 29, wherein Q is

wherein
R$_8$ is hydrogen, methyl, or ethyl,
wherein 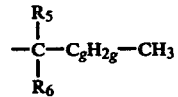 is

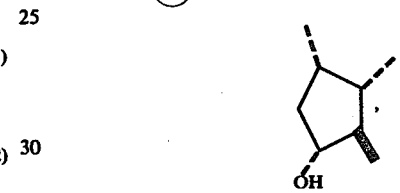

and wherein
R$_4$ is $$-\underset{R_6}{\overset{R_5}{C}}-C_gH_{2g}-CH_3$$

wherein
C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro.

31. (4E)-9-Deoxy-5,9α-epoxy-Δ$^4$-trans-Δ$^2$-PGF$_1$, methyl ester, a compound according to claim 30.

32. (4E)-9-Deoxy-5,9α-epoxy-Δ$^4$-trans-Δ$^2$-PGF$_1$, sodium salt, a compound according to claim 30.

* * * * *

UNITED STATES PATENT OFFICE
CERTIFICATE OF CORRECTION

Patent No. 4,202,972      Dated 13 May 1980

Inventor(s) Roy A. Johnson

It is certified that error appears in the above-identified patent and that said Letters Patent are hereby corrected as shown below:

Column 7, line 35, "40° C. In a solvent" should read -- 40° C. in a solvent --;

Column 8, line 26, "trans-66$^2$-PGF$_1$," should read -- trans-$\Delta^2$-PGF$_1$, --; line 41, "1.6" should read -- 1.6 M --;

Column 9, line 25, "prepared for the" should read -- prepared the --;

Column 13, line 9, "according to claim 1" should read -- according to claim 5 --; line 36, "according to claim 12" should read -- according to claim 6 --.

Signed and Sealed this

*Seventh* Day of *April 1981*

[SEAL]

*Attest:*

RENE D. TEGTMEYER

*Attesting Officer*     *Acting Commissioner of Patents and Trademark*